(12) United States Patent
Rutberg et al.

(10) Patent No.: US 8,956,157 B2
(45) Date of Patent: Feb. 17, 2015

(54) APPARATUS AND METHOD FOR TREATMENT OF PERIODONTAL DISEASE

(76) Inventors: Alexander Philippovich Rutberg, Madison, AL (US); Philipp Grigorevich Rutberg, Saint Petersburg (RU); Viktor Andreevich Kolikov, Saint Petersburg (RU); Galina Boricovna Shtorina, Saint Petersburg (RU); Harry D. Fair, Austin, TX (US)

( * ) Notice: Subject to any disclaimer, the term of this patent is extended or adjusted under 35 U.S.C. 154(b) by 0 days.

(21) Appl. No.: 13/361,969

(22) Filed: Jan. 31, 2012

(65) Prior Publication Data
US 2013/0196286 A1    Aug. 1, 2013

(51) Int. Cl.
*A61C 19/06* (2006.01)

(52) U.S. Cl.
USPC ............................... 433/32; 604/20

(58) Field of Classification Search
USPC .......................... 433/32, 80; 604/20
See application file for complete search history.

(56) References Cited

U.S. PATENT DOCUMENTS

| | | | | |
|---|---|---|---|---|
| 3,776,825 | A | * | 12/1973 | Vit ................................. 205/434 |
| 3,995,371 | A | * | 12/1976 | O'Keefe ..................... 433/217.1 |
| 4,149,533 | A | * | 4/1979 | Ishikawa et al. ................. 604/20 |
| 4,324,630 | A | * | 4/1982 | Sugita et al. ............. 204/192.12 |
| 5,464,513 | A | | 11/1995 | Goriachev |
| 6,153,210 | A | * | 11/2000 | Roberts et al. ................. 424/411 |
| 6,576,226 | B1 | | 6/2003 | Jernberg |
| 6,585,873 | B1 | | 7/2003 | Solomon et al. |
| 6,589,562 | B1 | | 7/2003 | Shefer et al. |
| 6,991,736 | B2 | * | 1/2006 | Downs .......................... 210/764 |
| 7,078,060 | B2 | | 7/2006 | Burrell et al. |
| 7,166,570 | B2 | | 1/2007 | Hunter et al. |
| 7,374,693 | B1 | | 5/2008 | Rutberg et al. |
| 7,413,667 | B1 | | 8/2008 | Routberg et al. |
| 7,713,955 | B2 | | 5/2010 | Whiteford et al. |
| 7,775,795 | B2 | * | 8/2010 | Khawaled et al. .............. 433/32 |
| 7,846,422 | B2 | | 12/2010 | Oshino |
| 8,290,579 | B2 | * | 10/2012 | Domb ............................. 604/20 |
| 2002/0132208 | A1 | * | 9/2002 | Magnani ........................ 433/80 |

(Continued)

FOREIGN PATENT DOCUMENTS

RU    2272697 C1    3/2006

OTHER PUBLICATIONS

Tien et al, Novel Technique for Preparing a Nano-Silver Water Suspension by the Arc-Discharge Method, Re.Adv.Mater.Sci. 18(2008) 750-756.*

(Continued)

*Primary Examiner* — Ralph Lewis
(74) *Attorney, Agent, or Firm* — File-EE-Patents.com; Jay A. Chesavage (57) ABSTRACT

An apparatus for the generation of metallic and metal oxide nanoparticles for use in the treatment of periodontal disease has a discharge chamber with a controlled flow of water, the water flowing through a plasma gap formed by electrodes, the electrodes having a pulsed voltage applied to create a plasma discharge, the pulse duration chosen to maximize the generation of nanoparticles from the electrodes which are in the range of 10 nm to 50 nm. The discharge chamber flow rate and pulse duration is controlled to maintain a particular temperature differential across the plasma gap to additionally optimize the nanoparticles population for the desired 10 nm to 20 nm size range having negative surface electric charge. The nanoparticles thereby formed may thereafter be applied to a subject in need thereof as an irrigation treatment, or as a paste applied directly to a region of periodontal disease.

26 Claims, 4 Drawing Sheets

(56) References Cited

U.S. PATENT DOCUMENTS

| | | |
|---|---|---|
| 2004/0007539 A1 | 1/2004 | Denes et al. |
| 2004/0168923 A1 | 9/2004 | Fang et al. |
| 2006/0070195 A1* | 4/2006 | Morita et al. .................... 15/105 |
| 2008/0187603 A1 | 8/2008 | Sawafta |
| 2009/0081312 A1 | 3/2009 | Block et al. |
| 2010/0206734 A1* | 8/2010 | Todd et al. ...................... 205/74 |
| 2010/0316685 A1 | 12/2010 | Willoughby |
| 2011/0262556 A1 | 10/2011 | Holladay et al. |
| 2011/0278178 A1 | 11/2011 | Pierce et al. |
| 2012/0021034 A1 | 1/2012 | Zink et al. |

OTHER PUBLICATIONS

PCT/US2013/023959 Search Report.

\* cited by examiner

*Figure 1*
Aqueous stream nanoparticle generator

*Figure 2*
Metal particle Generator with nanoparticle trap

*Figure 3*
Electrode feed mechanism

*Figure 4*
Anti-bacterial periodontal disease treatment film

*Figure 5*
Periodontal disease pocket treatment

*Figure 6*
Plasma Electrode Voltage and Current Plots

*Figure 7*
Plasma Pulsatile Power Supply

*Figure 8*
Electrode feed mechanism

*Figure 9*
Nanoparticle size distribution vs Pulse Duration

APPARATUS AND METHOD FOR TREATMENT OF PERIODONTAL DISEASE

FIELD OF THE INVENTION

The present invention relates to an apparatus and method for treating periodontal disease using metallic and metal oxide nanoparticles which have a physical size on the order of a fraction of the size of a pathogenic bacterium. In particular, the invention relates to the production and use of metallic and metal oxide nanoparticles in aqueous solution, having a size in the range of 10 nm to 50 nm and surface electric charge to increase their effectiveness against bacterium responsible for gingivitis and periodontal disease.

BACKGROUND OF THE INVENTION

Among the maladies that continue to afflict man and other animals are tooth decay and tooth loss. Both of these afflictions have been subjected to much study and application of dental therapeutic measures with various rates of success. One aspect of dental therapy that has received attention is the understanding of, and attempts at overcoming, periodontal disease. Periodontal disease is a general term that encompasses diseases that affect the gingiva or supportive connective tissue and alveolar bone which anchors the teeth in the jaws. A particular periodontal disease that can occur in individuals is periodontitis where connective tissue such as periodontal ligament tissue is lost, alveolar bone is re-absorbed, and periodontal pockets are formed. In more advanced stages of such a periodontal disease, teeth become loosened and may eventually be lost because of the compromised surrounding support structure. As the disease progresses, a gingival pocket which previously formed becomes deeper, and the alveolar bone is destroyed and absorbed. If this condition is left untreated, the affected tooth loses structural support and may fall out. With recent advancements in the treatment/prophylaxis of dental caries and the demographic movement towards an aging society, periodontal disease has attracted increased attention and its treatment has become an important subject. Severe periodontal disease requires reconstruction of the periodontal tissue by a surgical procedure. Its purposes are not only to remove the periodontal pocket but also to recover occlusive function through regeneration of the periodontal tissue destroyed by periodontal disease. Treatment of lost gum and bone tissue is challenging in the best case. For example, a representative corrective surgical technique currently performed is the gingival flap operation. However, postoperative recovery including true attachment accompanied by neogenesis of the cementum of the new attachment is typically limited only to the apical region, and ideal epithelial attachment is not achieved in other regions.

Periodontal diseases including periodontitis are caused by an accumulation of bacteria on the surface of the tooth and under the gingiva. Specific microorganisms that have been suggested as causative agents of periodontal disease are *Actinobacillus actinomycetemcomitans, Bacteroides forsythus, Campylobacter rectus, Eikenella corrodens, Fusobacterium nucleatum ss vincentii, Peptostreptococcus micros, Porphyromonas gingivalis, Prevotella denticola, Prevotella intermedia, Prevotella nigrescens, Streptococcus intermedius, Treponema denticola, Tannerella forsythia, Campylobacter gracilis* and *Actinomyces viscosus*. Mixtures of two or more microbial species may be present and cause, either individually or synergistically, periodontal disease.

Elimination of bacterial infection is key to the successful treatment of periodontal disease. It has been known for some time that silver compounds exhibit antimicrobial activity, which is known as the oligodynamic effect as discovered in 1893 by Karl Nageli. Silver sulfadiazine, when applied topically to the supra-gingival tooth surface in a gel base, has been shown both to prevent and to reduce gingival inflammation and plaque formation in beagle dogs (T. H. Howell et al., J. Periodontal Res. 25:197-200 (1990) and T. H. Howell et al., J. Clin. Periodontal. 17: 734-737 (1990)). Potential drawbacks to using silver compounds supra-gingivally in the treatment of periodontal disease are the staining of teeth and oral mucosa and the unpleasant taste that such treatment engenders. A potent, microbiocidally effective formulation that is locally applied subgingivally would provide a significant improvement in the treatment of periodontal disease.

U.S. Pat. No. 6,153,210 describes another treatment method for periodontal disease which uses metallic ionic compounds formed from silver chemically bonded to bromine, fluorine, chlorine, and others, to form any of the various compounds silver acetate, silver bromate, silver chlorate, silver perchlorate, silver chlorite, silver fluoride, silver lactate, silver permanganate, silver protein, silver nitrate, silver nitrite, silver sulfadiazine, silver sulfate or combinations of these chemical compounds and complexes. Of these chemical compounds and complexes, it is suggested in this patent that silver nitrate, silver chlorate, silver perchlorate and silver fluoride are preferred.

One of the problems in the delivery of metal ions at the chemical level is an interaction between the surface charge of the bacteria and the suspended metal ions, and this interaction causes a variation in the local concentration of metal ions. In particular, if the particular bacteria colony operative in the periodontal disease has a surface charge which is the same polarity as the naturally occurring positive ionic potential of the metal ions, the local concentration of the metallic ions in the area surrounding the bacteria will be reduced. It is desired to provide an apparatus for generation of aqueous solutions of nanoparticles of silver, copper, and iron, and in an optimum size range for use in treatment of periodontal disease. It is also desired to provide a method for application of nanoparticles for treatment of periodontal disease.

OBJECTS OF THE INVENTION

A first object of this invention is an apparatus for the generation of metallic and metal oxide nanoparticles for use in treating periodontal disease.

A second object of the invention is the modulation of a pulsed voltage generating a plasma to increase the yield of nanoparticles in the range of sizes 10-50 nm.

A third object of the invention is the generation of nanoparticles with surface electric charges which are attracted to bacterial pathogens, the surface electric charge provided by parameters associated with the applied pulsed voltage during plasma discharge.

A fourth object of the invention is a method for the generation of metallic and metal oxide nanoparticles for use in treating periodontal disease.

A fifth object of the invention is a treatment for periodontal disease comprising the mixture of a hardening agent which is mixed with nanoparticles in the 10-50 nm size range, the mixture applied to regions of periodontal disease in a subject in need thereof.

SUMMARY OF THE INVENTION

An apparatus for the generation of nanoparticles for treatment of periodontal disease includes a water channel supporting a water flow directed through a plasma formed in the gap between an anode and cathode in the water channel, the plasma generated from short pulses of voltage having a pulse duration in the range of 5-10 us, the pulses generated by a power supply which is optimized for the desired pulse duration and unipolar amplitude generation. The selection of pulse amplitude and duration creates a plasma across the anode electrode and cathode electrode gap, the plasma including nanoparticles of metal and metal oxide formed from the electrodes, where the pulse amplitude, polarity, and duration convey an electrostatic surface charge to the nanoparticles which is opposite to the polarity of the surface charge of the pathogenic bacteria, thereby encouraging the binding of nanoparticles to the pathogenic bacteria. In one example of the invention, a voltage on the order of 35 kV is applied across an electrode gap of 10 mm, with a delivery energy of 1 Joule per pulse, which is believed to be the optimal condition for generation of metallic and metal oxide nanoparticles from the electrodes and in the size range of 10 nm to 50 nm which provide highest effectiveness for the control of bacteria responsible for periodontal disease. Additionally, the flow rate of the water through the channel and electrode plasma gap is controlled to provide a fixed temperature increase across the water entering and leaving the plasma gap.

In one embodiment of the invention, the plasma is generated across a gap formed by metal electrodes which supports the water flow, and the generation of nanoparticles from the erosion of metal electrodes interacting with the plasma forms a suspension of the nanoparticles which is suitable for use in treatment of periodontal disease, such that the nanoparticle suspension may be subsequently used to irrigate a subject's gums which are in need of periodontal disease treatment. In another embodiment of the invention, the water suspension of nanoparticles is subjected to a subsequent concentration step, such as an evaporative or centrifugal step, resulting in the generation of a higher concentration of nanoparticles, or alternatively, a sorted size distribution of nanoparticles, which may be subsequently formed into a gel for topical application, a dissolving mouth rinse, in a pill form, or as a slurry or other dense suspension for use in a variety of topical applications for mixture with a paste to form a cream, or to inject directly into a pocket of periodontal disease activity. In another embodiment, the paste may be mixed with a hardening gel and injected into the affected gingivitis areas during treatment to provide an ongoing anti-bacterial agent over an extended time interval between treatments.

One example method for the treatment of periodontal disease uses the water suspension of nanoparticles produced by the apparatus of the invention, and includes the application of the water solution of nanoparticles in the size range 10 nm to 50 nm into the region of periodontal disease. The nanoparticles are dispensed to the affected area of a subject with periodontal disease and in need thereof, the nanoparticles in the form of a paste, an aqueous wash, or irrigated into a pocket of periodontal disease.

DETAILED DESCRIPTION OF THE INVENTION

The inventors believe that nanoparticles formed from metal ions (particularly silver ions), when provided in aqueous solution and with the nanoparticles having a size which is a fraction of the bacterium size the nanoparticles are delivered to neutralize, interfere with the function of peptidoglycan (or murein) of the plasma membrane of the bacterium cell wall. The metallic and metal oxide nanoparticles degrade the bacterium membrane's ability to transfer oxygen, leading to bacterium cell death and providing the desired antibacterial properties. Functionally operative nanoparticles have a size for use with gingivitis and associated periodontal bacteria in the range 10-50 nm with a preferred nanoparticle size range of 10-20 nm and in an aqueous concentration range of 10-80 mg of metallic and metal oxide nanoparticles per liter of water.

Figure 1:
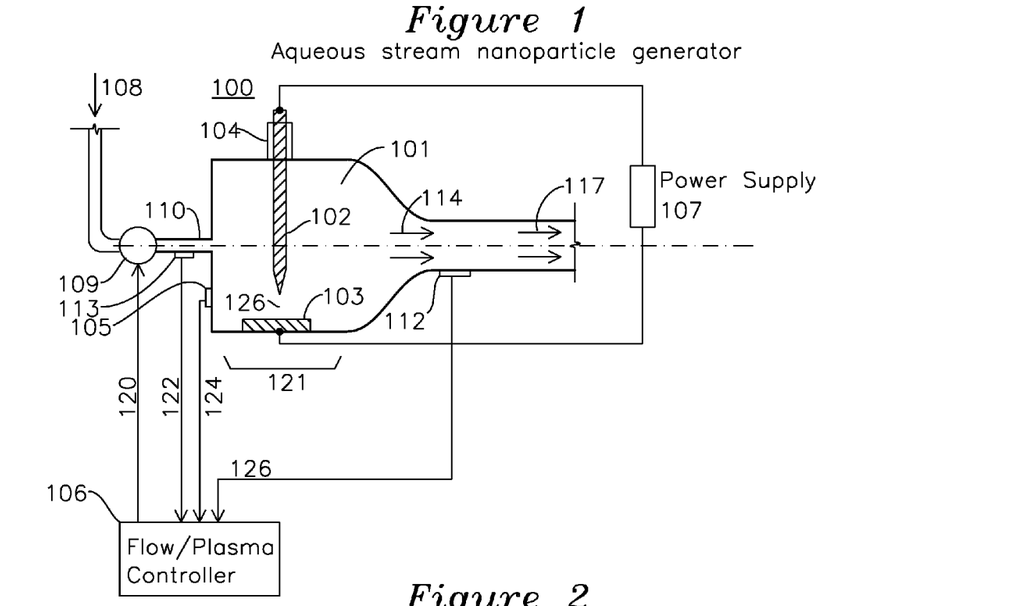
FIG. 1 is a diagram for an apparatus which generates a continuous flow of metallic and metal oxide nanoparticles in solution.

FIG. 1 shows an example embodiment of a nanoparticle generator 100 according to one aspect of the invention. The dimensions may vary widely from one example device to another, and in the present example, a size reference to "on the order of" means the particular dimension or value may vary by a factor of 10 greater or smaller than the reference value without loss of generality, and these values may also be extended above or below the order of magnitude limitation suggested earlier. It is understood that plasma physics devices of the type described herein may be fabricated in any scaled size which maintains central parameters such as energy level and voltage value for a given configuration. Example values are given only for understanding the structures and functions of the invention, and are not intended to limit the invention to only those values or ranges of values described.

The nanoparticle generator 100 can be provided in several different forms, and is shown in FIG. 1 to provide a steady stream of nanoparticles in water solution for the treatment of periodontal disease such as in the dental office setting by delivery of a continuous source of nanoparticles in an irrigation solution. As will be described later, the device 100 can also be modified to generate metallic and metal oxide nanoparticles which may be subsequently concentrated such as with the use of a centrifuge or evaporator, and the concentrated form thereby produced may be suitable for the generation of metallic and metal oxide nanoparticles containing treatment pastes, fluxes, creams, surface coatings, or pills for topical or other uses in a setting of the patient's convenience.

In one example embodiment for the generation of a continuous stream of nanoparticles in a water solution, inlet 108 is coupled to a source of water which may be regulated for flow volume in the channel 101 to a rate on the order of 7.5 liter/hour (125 cc/min) and, for a channel cross section of 0.8 $cm^2$, this results in a linear flow of 160 cm/min, using pump 109 to inlet 110, which includes inlet water temperature measurement sensor 113. In a preferred embodiment, the channel 101 diameter is on the order of 10 mm, the water is deionized or distilled and is provided through a channel extent 121 in the axial direction of aqueous flow on the order of 20 mm which forms chamber 101 with the 20 mm axial extent 121 including the plasma generation arc formed by a cathode electrode 102 and an anode electrode 103 which are electrically coupled to power supply 107 for provision of a pulsed voltage on the order of 35 kV which causes a plasma discharge to form across the anode to cathode plasma gap 126 which may be on the order of 10 mm. The cathode electrode 102 may be a metal wire with a diameter on the order of 1 mm, and the electrode 102 may be formed from a metal such as silver, copper, iron, or any alloy containing silver, copper, or iron. In one embodiment of the invention shown in FIG. 3 and described later, the cathode 102 is a wire electrode with a feed rate on the order of 3 mm/hr. The anode electrode 103 may be fabricated from a plate of the same metal as the cathode 102 and having a greater diameter than the cathode electrode 102 wire to reduce the wear rate of the anode electrode 103, or alternatively the anode 103 may also be fabricated from a wire conductor composed of the same material as the cathode electrode 102. A feed control mechanism 104 may provide a linear feed of electrode 102 to maintain a constant gap 126 and the power supply 107 may provide a pulsed voltage on the order of 35 kV. In general, the anode is coupled to a positive terminal, and the cathode to a negative terminal of the power supply 107. Many different feed mechanisms are possible, one of which is shown in FIG. 3 with a spool of wire and feed rollers.

Figure 3:
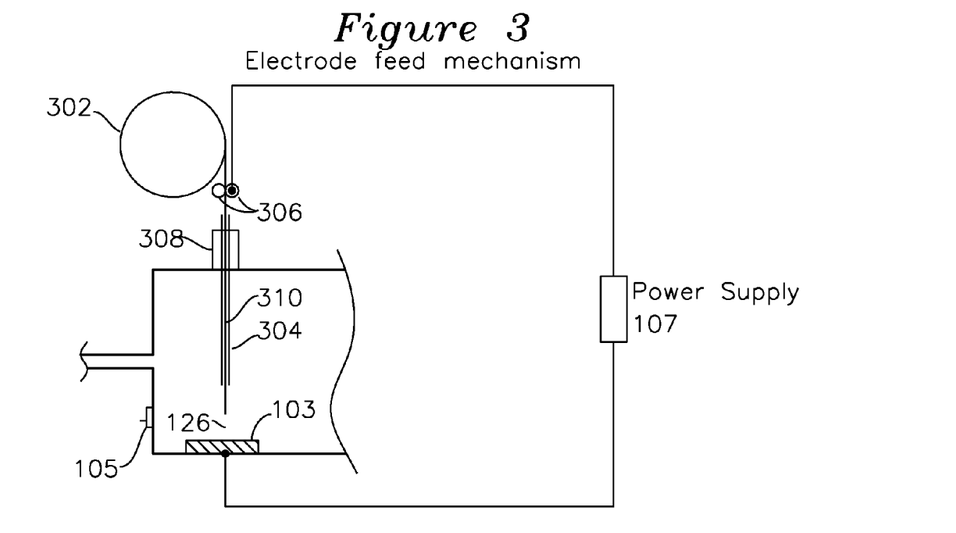
FIG. 3 is a diagram of an electrode feed mechanism.
Figure 8:
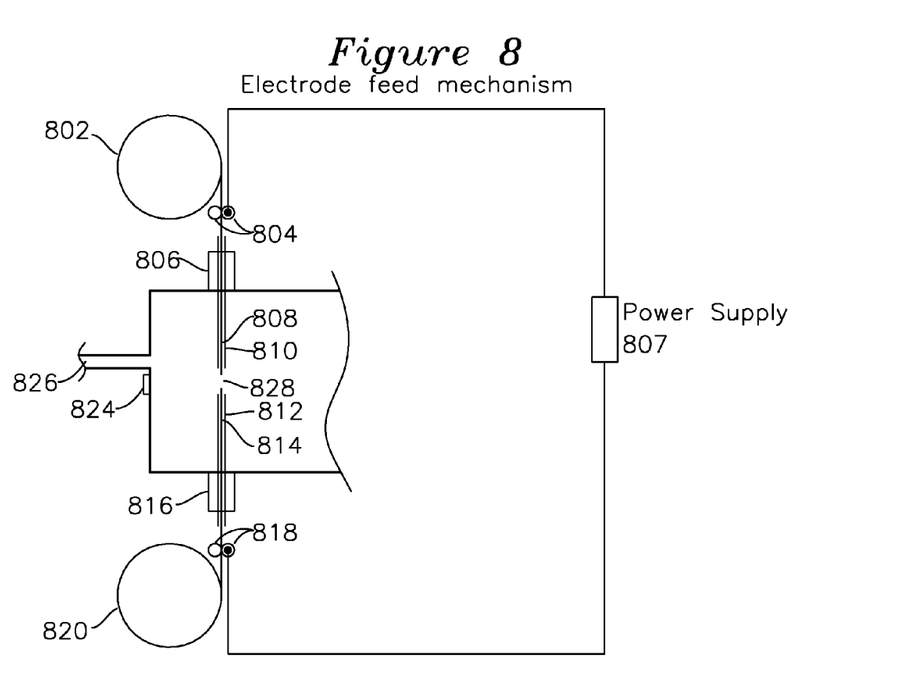
FIG. 8 is a diagram of a dual wire electrode feed system.

FIG. 3 shows an embodiment for a wire feed mechanism where silver, copper, iron, or an alloy of silver, copper, or iron, is provided in wire form and wrapped into spool 302, which is driven by feed rollers 306 which are also in pressure and electrical contact, and coupled to power supply 107 to form plasma arc 126 with anode electrode 103, as was described in FIG. 1. Guide 304 may be an insulating material which is supported and separated from the water channel by gasket and support 104. A photo sensor 105 may be placed in optical range of plasma gap 126 to monitor the optical irradiation of the formed plasma for communication to the controller 106 of FIG. 1 for electrode feed control of feed rollers 306 and to re-establish a plasma such as by momentarily reducing the plasma gap 126 by feeding additional electrode material into the plasma gap until the plasma initiates and nanoparticles form. The plasma gap may subsequently be adjusted to optimize the formation of nanoparticles with a particular size distribution. FIG. 8 shows another electrode configuration embodiment of the invention with water inlet 826 where the plasma gap 828 is developed by anode electrode 808 and cathode electrode 814, which are provided as wires guided by insulating guides 810 and 812, respectively, stored in feed spools 802 and 820, respectively, and electrically energized by feed rollers 804 and 818, respectively, which are electrically connected to power supply 107, as before. In this configuration, where wire electrodes 808 and 814 have an example diameter on the order of 1 mm and a plasma gap on the order of 10 mm, the feed rate of the anode electrode is on the order of 6.6 mm/hr, and the feed rate of the cathode electrode is on the order of 3.3 mm/hr. Sensor 824 may be used to evaluate the presence of plasma formed in plasma gap 828. The anode and cathode wires in such a configuration may be the same diameter, or different diameters, since when the wires are the same diameter, the linear consumption rate of the anode wire is approximately twice the linear consumption rate of the cathode.

Returning to FIG. 1, the water flow rate at inlet 108 is controlled via pump 109 by flow/plasma controller 106 to regulate the flow 108 through the plasma gap 126 to provide a difference in temperature from outlet thermal sensor 112 to inlet thermal sensor 113 less than of approximately 7° C., which is believed to provide the highest yield of desired 10 nm to 20 nm size nanoparticles, while the incoming inlet water temperature as measured by sensor 113 may vary anywhere in the range 5° C. to 50° C., as is possible for a particular distribution of nanoparticles by size in the particular nanoparticle generator 100. In one embodiment of the invention, the parameter of temperature differential across the plasma gap, the parameter of water flow through the plasma gap, the parameter of voltage duration which is applied to the plasma, or parameter of repetition rate of the voltage generated by the power supply, or any combination of these parameters is selected to cause the majority of metallic or metal oxide nanoparticles formed by the plasma to be in either the size range of 10 nm to 20 nm, or in the size range of 10 nm to 50 nm. It has been observed that nanoparticles from 5 nm to 300 nm are formed when the temperature difference is allowed to vary widely or tend to higher temperatures, whereas close control the temperature differential from plasma flow outlet to plasma flow inlet across extent 121 to less than 7° C. results in greatly improved yield of the desired nanoparticles for treatment of periodontal disease in the range 10 nm to 50 nm.

Figure 2:
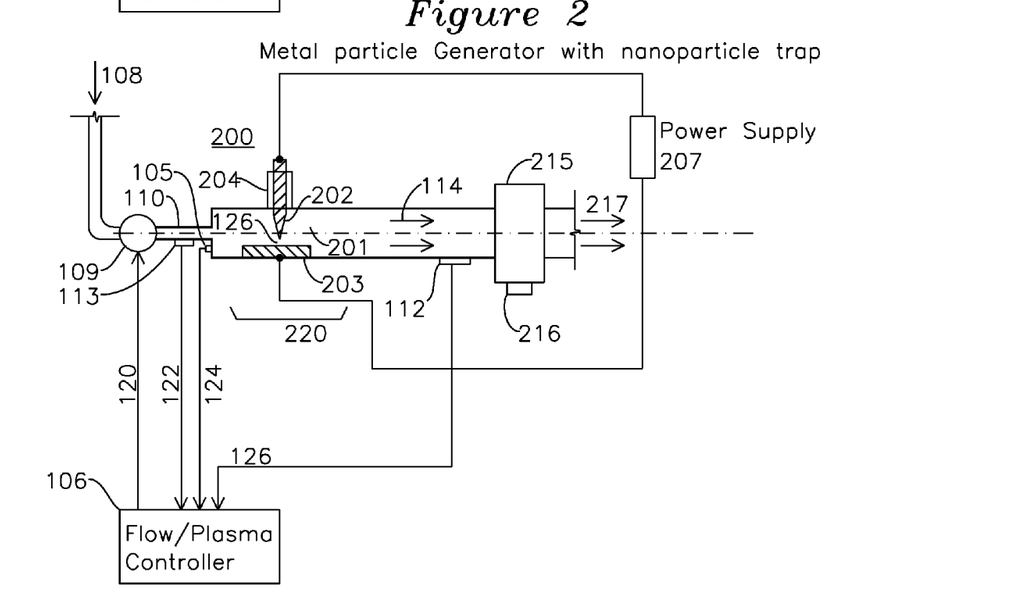
FIG. 2 is a diagram for an apparatus which generates metallic and metal oxide nanoparticles in water solution which are harvested from the water solution using a particle concentrator.

FIG. 2 shows an embodiment for a nanoparticle generator 200 for generation of concentrated solutions of nanoparticles, such as for use in subsequent mixture of the concentrated density nanoparticles with binding agents, films, or to dispense in creams or hardening agents for direct injection into the periodontal disease site requiring antibacterial action. The generator 200 of FIG. 2 includes inlet 108 coupled to a source of preferably deionized or distilled water, a pump 109 which regulates the flow through the channel 201, and cathode 202 forming a plasma gap 126 with anode electrode 203 and generating an outflow 114 of nanoparticles. The outflow 114 is provided to concentrator 215 such as a centrifuge or evaporative region where nanoparticles may be separated by weight or by increasing their density by reducing the volume of water suspension agent. In an efficiently operating system, the outlet 114 flow into the concentrator 215 contains a significantly higher concentration of nanoparticles than the outflow 217 leaving the concentrator 215. The nanoparticles which are collected 216 may be used to provide the anti-bacterial nanoparticles for periodontal treatment as a film with a removable adhesive layer for direct application to the teeth and gums, a cream for optical use, or a temporarily or permanently applied composite such as a hardening agent which includes a nanoparticles added provided from collection area 216. Concentrator 215 may alternatively be a centrifuge where centripetal force from axial rotation causes the nanoparticles to collect in higher concentrations in the outer region of the rotating centrifuge and subsequently collected for use in forming treatment creams, pastes, or suspensions.

Figure 4:
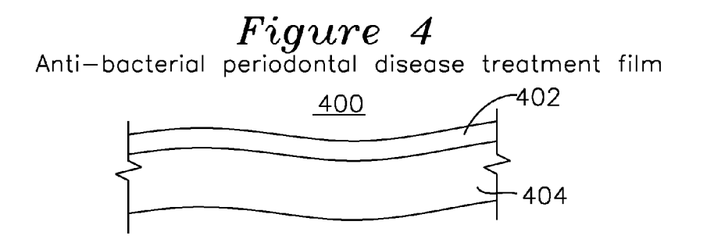
FIG. 4 is a diagram of a flexible substrate with an antibacterial nanoparticle film applied for use on teeth for treating periodontal disease.

FIG. 4 shows a periodontal disease treatment film 400 which comprises a film substrate layer 402 supporting an anti-bacterial layer 404 which includes binder agents, an optional adhesive mixture, and the nanoparticles from collector 216 of FIG. 2. The film 400 may be placed on teeth with periodontal disease such that the periodic release of antibacterial nanoparticles to the surrounding gum and tooth margin tissue areas reduces the bacteria level.

Figure 7:
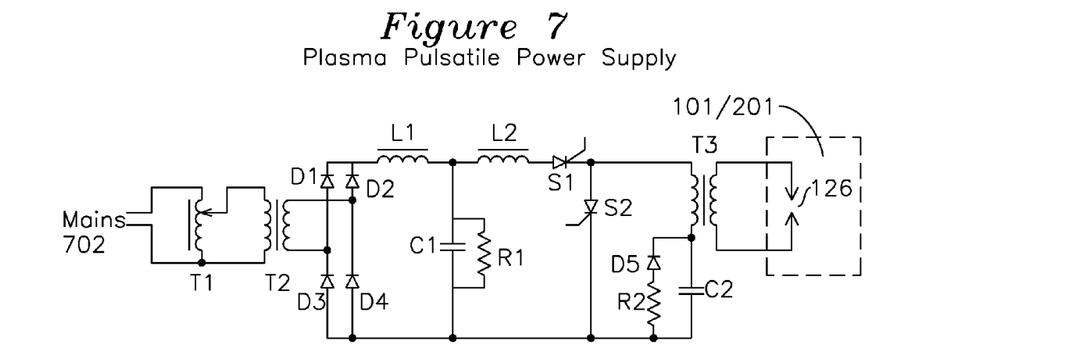
FIG. 7 is the schematic diagram of a power supply.

FIG. 7 shows an example power supply 107 of FIG. 1 or 3, 207 of FIG. 2, or 807 of FIG. 8. Mains voltage 702 is applied to variable transformer T1 which generates a controllable AC voltage to T2, and rectifier diodes D1, D2, D3, D4 produce rectified DC to filter L1 and C1, which charges to a peak voltage Vp. Inductor L2 limits peak current when switch S1 closes and charges C2 to Vp. After C2 is charged to Vp, switch S1 optionally opens and switch S2 closes, which discharges energy storage capacitor C2 through T3 and S2. Clamp diode D5 ensures that a single sinusoidal cycle of current is delivered based on the self-resonant frequency of self inductance of T3 in combination with capacitance of C2. In the best mode for generation of maximum distribution of nanoparticles in the 10-50 nm range, the sinusoidal half cycle period is less than 10 us. In one embodiment of the invention, the repetition rate of the pulsatile voltage generated by power supply T3 which forms the plasma is 50 Hz or more. Switch elements S1 and S2 are shown for simplicity as SCR (or triac) elements without a gate control, however the switch control and switch elements may be achieved in any manner which provides the desired plasma current and polarity characteristics.

Figure 6:
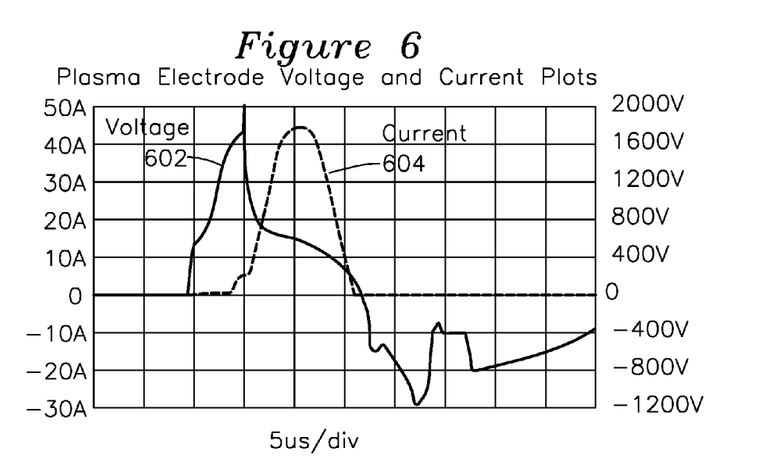
FIG. 6 is a plot of the current and voltage across the plasma gap.

FIG. 6 shows example voltage and current developed across the anode electrode and cathode electrode by the power supply of FIG. 7. Waveform 602 shows the applied voltage at 10 us from the start of the plot. In the absence of plasma formation or plasma electrodes and associated plasma gap, the instantaneous open circuit voltage generated by FIG. 7 may be 35 KV. The plot of FIG. 6 shows plasma voltage developed across the electrodes, which is limited to a few thousand volts, with plasma formation occurring at approximately 600V, and the current waveform 604 indicates the typical time lag associated with sinusoidal current development starting just before 15 us, with the cycle time derived from the circuit inductance and capacitance as previously described, and returning to baseline at approximately 26 us from start of the plot. FIG. 6 is understood to be an example plot which shows one example of plasma breakdown upon application of 35 kV (with the plot extents shown only to 2000V) across a 10 mm electrode gap, a peak current of 45 A, and a single cycle of current carrying only a substantially positive current pulse, thereby creating nanoparticles from the electrodes with negative surface charge.

Figure 9:
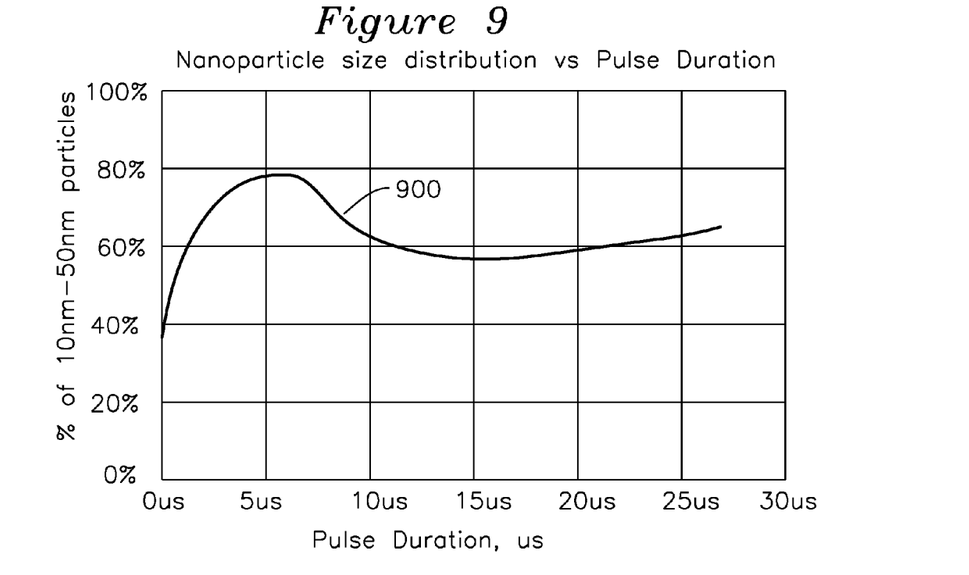
FIG. 9 is a plot of the yield of particles in the desired 10 nm-50 nm range as a function of pulse duration.

FIG. 9 shows a plot 900 of the fractional yield of nanoparticles in the desired 10 nm to 50 nm range as a function of pulse duration. As can be seen from the plot, a pulse duration less than 10 us is desirable, with an optimal pulse duration range of approximately 3 us to 7 us.

Figure 5:
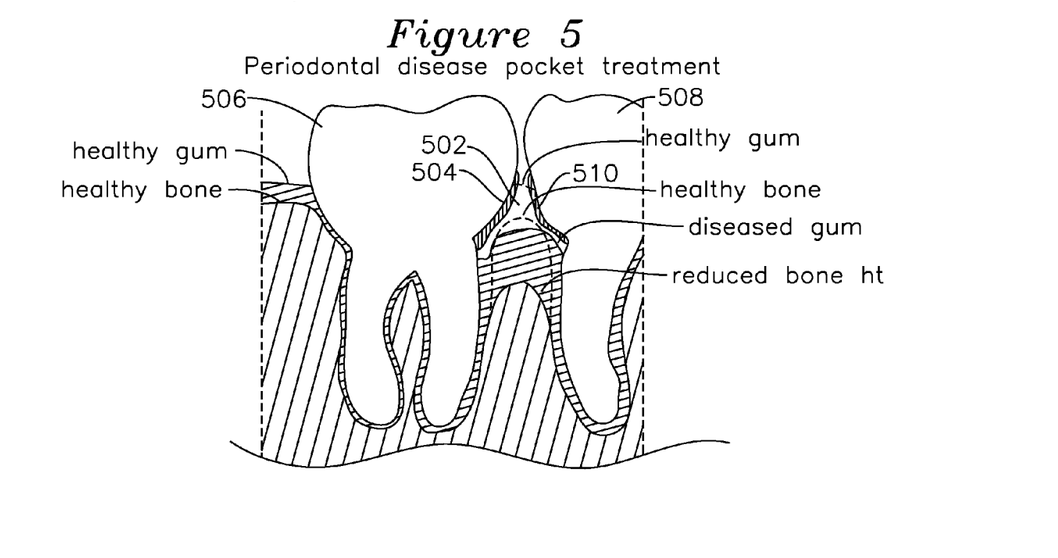
FIG. 5 is a diagram of a treatment method for periodontal disease using a hardening film and silver nanoparticles according to the present invention.

FIG. 5 shows an example of the invention where a hardening gel 504, 510 is applied to adjacent teeth 506, 508 of a subject with periodontal disease. The original healthy gum margin and healthy bone regions are shown in dashed lines, with the current gum and bone regions marked as indicated. The exposure of tooth root structure and gum retreat is associated with disease pocket 502, which is treated using a coating 504 of hardening agent mixed with nanoparticles and applied in regions of periodontal disease as shown, where the slow and continuous release of antibacterial nanoparticles may arrest the progression of gingivitis and bone loss in the periodontal disease pocket.

For the generators 100 and 200 of FIGS. 1 and 2, another process step is taken to maximize the efficacy of the nanoparticles which are generated according to these methods. In addition to the control of parameters which optimize the plasma generation of the nanoparticles in the 10-50 nm range, it is further desired to increase the antibacterial efficacy of the nanoparticles as antibacterial agents by providing a surface electric charge to the surface of the nanoparticles generated by the plasma arc 126 of FIGS. 1 and 2. The surface electric charge on the nanoparticles thereby provides an electrostatic attraction between the nanoparticles generated and the bacteria which are intended to be destroyed by the nanoparticles, and the surface electric charge of the nanoparticles creates an attraction to the bacteria which is significantly stronger than the natural ionic charge of the metallic ions of nanoparticles.

The optimization of surface electric charge applied to the generated nanoparticles is accomplished by pulsing the power supply 107 to generate a current through the electrode gap 126 of duration 5-10 us and using a pulse polarity with a sign opposite the bacteria surface charge. In this manner, the nanoparticles with a negative charge which are formed from the electrodes are placed into suspension, and this charge causes the nanoparticles to better adhere to the gingivitis forming bacteria which tend to have a positive surface potential, resulting in improved anti-bacterial action.

The inventors performed a series of clinical trials of the technique on a series of subjects, measuring the bacterial load range of common bacteria responsible for periodontal disease. As a summary of the effectiveness of the treatment, the table below shows the maximum bacterial density found before irrigation treatment with nanoparticles generated by the device 100 of FIG. 1 or 200 of FIG. 2 compared with the maximum bacterial loads after treatment.

| common name | Bacteria name | Max Bacterial load range before treatment (cm$^{-3}$) | Max Bacterial load range after treatment (cm$^{-3}$) |
|---|---|---|---|
| Acti. acti | Aggregatibacter actinomycetemcomitans | $10^3$ | 0 |
| P. gin | Porphyromonas gingivalis | $10^7$ | 0 |
| Pr. int | Prevotella intermedia | $10^3$ | $10^4$ |
| T. for | Tannerella forsynthia | $10^3$ | 0 |
| Tr. dent | Treponema denticola | $10^3$ | 0 |

In one method of treatment, the aqueous solution of nanoparticles is directly irrigated over the effected area for several minutes including a syringe irrigation of the periodontal pockets. The periodontal pockets are subsequently sealed with a dressing material such as VOCO-PACK®, Visco-Gel®, or any of several different types of equivalent soft removable sealants to maintain the nanoparticles in the periodontal pocket. In one embodiment of the process, the dressing material such as VOCO-PACK or Visco-Gel is used in powder form and mixed with the nanoparticle aqueous solution generated by FIG. 1, or the higher concentration aqueous solution generated by FIG. 2, such that the nanoparticle aqueous solution and powder dressing material work together to enhance the treatment effectiveness and duration of antibacterial nanoparticle application. The process of irrigation and temporarily sealing the site was done in 3-4 sessions every 2-3 days, resulting in the reduction of bacteria levels as shown in the table above.

Many variations of the process and apparatus may be practiced, and the examples provided are only for understanding the invention. The electrode gap may be any gap which supports plasma generation, such as in the order of magnitude range of 60V per mm of electrode gap. The anode electrode may provide more of the nanoparticles in suspension than cathode electrode, where more of the nanoparticles is understood to be more than 60% of the nanoparticles by count.

We claim:

1. An apparatus for the generation of an aqueous stream of metallic and metal oxide nanoparticles, the apparatus having:
   a discharge chamber supporting a flow of water;
   an anode electrode placed along one surface of said discharge chamber;
   a cathode electrode placed opposite said anode electrode and a plasma gap distance from said anode electrode, said cathode electrode and anode electrode coupled to a power supply having a voltage sufficient to generate a plasma across said plasma gap;

a flow controller which regulates said flow of water to a rate sufficient to result in a constant temperature difference of less than 7 degrees Celcius between the water temperature entering said plasma gap and the water temperature exiting said plasma gap;

said power supply providing a pulsed voltage applied to form said plasma in said flow of water and said temperature difference of less than 7 degrees Celcius is selected for a particular temperature which generates said nanoparticles from said cathode electrode and said anode electrode in the size range from 10nm to 50nm and with a fractional yield in said 10nm to 50nm size range greater than 50%.

2. The apparatus of claim 1 where said power supply pulsed voltage has an amplitude, polarity and duration selected to generate nanoparticles with a surface electric charge which is opposite the surface electrical charge of a targeted bacterium.

3. The apparatus of claim 1 where said plasma pulsed voltage is applied to unipolar cycles of plasma current, each said unipolar cycle having a duration less than 10 us.

4. The apparatus of claim 1 where the voltage applied to said plasma gap is at least 60V per mm of said plasma gap.

5. The apparatus of claim 1 where said pulsed voltage is a unipolar pulse formed by the secondary winding of a transformer, said transformer having a primary winding which is in series with a capacitor and forming a series resonant circuit with a half cycle resonance of less than 10 us, said series resonant circuit in series with a charged capacitor and a switch, said series resonant circuit also in parallel with a clamp, where upon closure of said switch, said series resonant circuit generates a half-cycle pulse to said cathode electrode and said anode electrode having a duration of less than 10us during a first duration, and said clamp suppresses the generation of opposite polarity current during a subsequent duration.

6. The apparatus of claim 1 where at least one of said anode electrode or said cathode electrode is a wire with a feed mechanism to replace electrode material consumed from said nanoparticle generation.

7. The apparatus of claim 1 where said pulsed voltage duration is selected to generate said nanoparticles with negative electric surface charge.

8. The apparatus of claim 1 where the majority of said nanoparticles from said anode electrode and said cathode electrode are generated with a size range of 10 nm to 50 nm.

9. The apparatus of claim 1 where said anode electrode and said cathode electrode are both wire electrodes and said plasma gap is formed by the gap between said wire electrodes.

10. A nanoparticle generator for treatment of periodontal disease, the generator having:
a channel enclosing a water flow, said channel supporting an anode electrode and a cathode electrode oriented perpendicular to the water flow in said channel, said anode electrode and said cathode electrode separated by a plasma gap and coupled to a pulsed voltage;
a nanoparticle trap for capturing resultant nanoparticles;
said channel regulating the rate of flow of said water to maintain a temperature increase in the water flow caused by a plasma formed in said plasma gap, said temperature increase regulated to a value less than 7 degrees Celcius;
said anode electrode generating a greater mass of nanoparticles than said cathode electrode;
said regulation of rate of flow, said pulse amplitude, said pulse duration causing the generation of nanoparticles having greater than 50% fractional yield of sizes in the range from 10 nm to 50 nm;
said pulse voltage generated by a resonant circuit generating a unipolar half-cycle of current with a duration of less than 10 us;
said nanoparticles having an electrical charge attractive to a bacterium.

11. The nanoparticle generator of claim 10 where said cathode electrode and said anode electrode are wire electrodes coupled to a feed mechanism which regulates the extent of said plasma gap.

12. The nanoparticle generator of claim 10 where either the repetition rate of said pulsed voltage or the rate of flow of said water is governed to provide a particular temperature increase from water entering said plasma gap and water exiting said plasma gap.

13. The nanoparticle generator of claim 10 where said pulsed voltage is formed by the output of a transformer coupled to said anode electrode and said cathode electrode, and where the input of said transformer is coupled to a storage capacitor in series with a switch element.

14. The nanoparticle generator of claim 13 where said switch element is operated to produce a substantially sinusoidal half cycle pulse of current from said anode to said cathode.

15. The nanoparticle generator of claim 10 where the water flow which exits said plasma gap contains nanoparticles which are applied to a concentrator which increases the density of said nanoparticles.

16. The nanoparticle generator of claim 10 where said nanoparticles are formed into a paste, an aqueous wash, or irrigated into a pocket of periodontal disease in a subject in need thereof.

17. A method for the treatment of periodontal disease, the method having the steps:
a nanoparticle generation step of generating nanoparticles with a size distribution, whereby nanoparticles in the range of 10 nm to 50 nm represent 50% or more of said nanoparticles in said size distribution, said nanoparticles generated from a plasma arc with an arc voltage of approximately 800 volts and an arc current of approximately 40 amps;
said nanoparticles having an electrical charge opposite the electrical charge of a bacteria;
an application step of applying said nanoparticles to areas of periodontal disease bacteria in a patient in need thereof.

18. The method of claim 17 where said nanoparticles surface electrical charge is opposite the surface electrical charge of periodontal disease bacterium.

19. The method of claim 17 where said nanoparticle generation step utilizes the discharge of a plasma from an anode electrode to a cathode electrode, the cathode electrode providing more of said nanoparticles than said anode electrode.

20. The method of claim 19 where said anode electrode and said cathode electrode provides all of said nanoparticles.

21. The method of claim 17 where said application is the direct irrigation of an area of the subject using nanoparticles generated by a nanoparticle generator.

22. The method of claim 17 where said application is the mixture of said nanoparticles in suspension with a gel or hardening agent which is subsequently applied to a subject in need thereof.

23. The method of claim 17 where said application is a mixture of VOCO-PACK, Visco-Gel, or an equivalent soft sealant and a suspension of nanoparticles in water.

24. The method of claim 17 where said nanoparticles are silver and silver oxides.

25. The method of claim 17 where at least one of said anode electrode or said cathode electrode is formed from one or more of silver, copper, iron, or an alloy containing silver, copper, or iron.

26. The method of claim 17 where said application is a film having a substrate layer which has applied an adhesive mixed with nanoparticles, the film for application to the subject in need thereof.

* * * * *